(12) United States Patent
Mikkaichi

(10) Patent No.: US 8,353,920 B2
(45) Date of Patent: Jan. 15, 2013

(54) SUTURE INSTRUMENT

(75) Inventor: Takayasu Mikkaichi, Tokyo (JP)

(73) Assignee: Olympus Corporation (JP)

( * ) Notice: Subject to any disclaimer, the term of this patent is extended or adjusted under 35 U.S.C. 154(b) by 966 days.

(21) Appl. No.: 11/734,429

(22) Filed: Apr. 12, 2007

(65) Prior Publication Data

US 2007/0185503 A1 Aug. 9, 2007

Related U.S. Application Data

(63) Continuation of application No. PCT/JP2006/303900, filed on Mar. 1, 2006.

(30) Foreign Application Priority Data

Mar. 17, 2005 (JP) ................................ P2005-076949

(51) Int. Cl.
*A61B 17/04* (2006.01)
*A61B 1/00* (2006.01)

(52) U.S. Cl. .......................... 606/145; 606/148; 600/104

(58) Field of Classification Search .................. 606/139, 606/144, 145, 148; 600/104
See application file for complete search history.

(56) References Cited

U.S. PATENT DOCUMENTS

| | | | |
|---|---|---|---|
| 3,470,875 A | 10/1969 | Johnson | |
| 3,946,740 A * | 3/1976 | Bassett | 606/145 |
| 5,728,112 A | 3/1998 | Yoon | |
| 5,797,927 A | 8/1998 | Yoon | |
| 6,322,570 B1 * | 11/2001 | Matsutani et al. | 606/148 |
| 7,063,715 B2 * | 6/2006 | Onuki et al. | 606/139 |
| 7,736,374 B2 * | 6/2010 | Vaughan et al. | 606/144 |
| 2002/0156344 A1 | 10/2002 | Pasricha et al. | 600/113 |
| 2003/0236535 A1 | 12/2003 | Onuki et al. | 606/144 |
| 2004/0138682 A1 | 7/2004 | Onuki et al. | 606/144 |

FOREIGN PATENT DOCUMENTS

| | | |
|---|---|---|
| JP | 59-21775 | 6/1984 |
| JP | 05-237123 | 9/1993 |
| JP | 10-192290 | 7/1998 |
| JP | 2000-37390 | 2/2000 |
| JP | 2002-330973 | 11/2002 |
| JP | 2002-336263 | 11/2002 |
| JP | 2003-305046 | 10/2003 |
| JP | 2004-601 | 1/2004 |
| JP | 2004-41733 | 2/2004 |

OTHER PUBLICATIONS

Office Action issued by the Chinese Patent Office on Oct. 31, 2008 in connection with corresponding Chinese Patent Application No. 200680008047.6.

(Continued)

*Primary Examiner* — Julian Woo
(74) *Attorney, Agent, or Firm* — Ostrolenk Faber LLP

(57) ABSTRACT

A suture instrument includes a gripping portion that grips a plurality of tissue pieces by sandwiching them, and a suture needle that punctures and sutures the plurality of tissue pieces, the suture needle is supported so as to be able to move forwards or backwards relative to the gripping portion, and a direction of the forward or backward movement of the suture needle is set in a direction that intersects the tissue pieces gripped by the gripping portion.

1 Claim, 15 Drawing Sheets

OTHER PUBLICATIONS

Translation of the Office Action issued by the Chinese Patent Office on Oct. 31, 2008 in connection with corresponding Chinese Patent Application No. 200680008047.6.

International Search Report PCT/JP2006/303900 dated May 23, 2006.

Office Action issued by the Japanese Patent Office on Jun. 14, 2011 in connection with corresponding Japanese Patent Application No. 2007-508062.

Translation of the Office Action issued by the Japanese Patent Office on Jun. 14, 2011 in connection with corresponding Japanese Patent Application No. 2007-508062.

Office Action issued by the Japanese Patent Office on Jan. 17, 2012 in connection with corresponding Japanese Patent Application No. 2007-508062.

Translation of the Office Action issued by the Japanese Patent Office on Jan. 17, 2012 in connection with corresponding Japanese Patent Application No. 2007-508062.

\* cited by examiner

SUTURE INSTRUMENT

CROSS REFERENCE TO RELATED APPLICATION

The is a continuation application of PCT/JP2006/303900 filed Mar. 1, 2006 which claims priority to Japanese Patent Application 2005-076949 filed Mar. 17, 2005, which is hereby incorporated by reference. The PCT International Application was published in the Japanese language.

TECHNICAL FIELD

The present invention relates to a suture instrument that is used when suturing a piece of tissue.

BACKGROUND ART

In recent years, in the field of medicine and the like, treatment tools for an endoscope are used in order to perform various treatments inside a body cavity using an endoscope. Among these, treatment tools for an endoscope are known that have a sheath that extends in a cylindrical shape, a gripping portion that is supported so as to be able to move forwards and backwards inside the sheath, and a needle portion that is supported so as to be able to move forwards and backwards inside the sheath and coaxially with the gripping portion (see, for example, Patent Document 1).

In addition, this needle portion is formed in a cylindrical shape and a T-bar that is connected to a connecting thread is inserted in a cylinder hole of the needle portion.

Based on a structure such as this, when a biological tissue portion in the form of a thin membrane is gripped by the gripping portion, if the needle portion is moved forwards relative to the gripping portion, then the needle portion punctures the biological tissue. While the needle portion is puncturing the biological tissue, the T-bar is pushed into the biological tissue. By then pulling the connecting thread, the T-bar is pressed against the internal side of the biological tissue so that a portion of the biological tissue is made to protrude outwards towards the surgeon. This protruding portion is then excised.

Moreover, conventionally, when suturing a plurality of tissue pieces, a suturing instrument is used that sutures a plurality of tissue pieces using a needle and thread, or that clamps together a plurality of tissue pieces using clips.

Patent Document 1 Japanese Unexamined Patent Application, First Publication No. 2002-330973.

It is an object of the present invention to provide a suture instrument that makes it possible to reliably suture a plurality of tissue pieces, and to greatly reduce a burden on a patient.

DISCLOSURE OF INVENTION

The present invention provides the following devices in order to solve the above described problems.

The present invention includes a gripping portion that grips a plurality of tissue pieces by sandwiching them, and a suture needle that punctures and sutures the plurality of tissue pieces, the suture needle is supported so as to be able to move forwards or backwards relative to the gripping portion, and the direction of the forward or backward movement of the suture needle is set to a direction that intersects the tissue pieces gripped by the gripping portion.

Note that the term 'plurality of tissue pieces' includes, for example, not only tissue pieces such as creases that are each formed separately and exist independently, but also, for example, two tissue pieces of which a portion is separated by an opening or the like, and that face each other across this opening. Namely, 'a plurality of tissue pieces' refers to tissue pieces of which at least a portion is separated.

Moreover, the present invention includes a gripping portion having gripping surfaces that grip a plurality of tissue pieces by sandwiching them, and a suture needle that punctures and sutures the plurality of tissue pieces, the suture needle is supported so as to be able to move forwards or backwards relative to the gripping portion, and the direction of the forward or backward movement of the suture needle at least when it is puncturing the tissue pieces is set to a direction that intersects a plane containing the gripping surfaces.

Note that the term 'at least' refers here to this intersection not being essential at times other than when a plurality of tissue pieces are being punctured by a suture needle, for example, when the gripping portion and the suture needle are being inserted in a body cavity, or when the gripping portion and suture needle have been inserted into a body cavity and the two are in the process of being moved towards a plurality of tissue pieces, and this intersection is only required during the actual puncturing.

In the present invention it is also possible for the gripping portion to be provided with gripping pieces on which the gripping surfaces are respectively provided, these gripping pieces are able to move in a direction in which they approach each other and in a direction in which they move apart from each other, and when these gripping pieces are made to approach each other and grip the tissue pieces via the gripping surfaces, at least one of the gripping surfaces may placed at a position facing the suture needle.

In the present invention it is also possible for the suture needle to be located on substantially the same plane as a plane containing a virtual line that extends in a direction in which the plurality of gripping pieces move towards or apart from each other, and an axis that extends in the direction of forward or backward movement of the suture needle, and, taking one gripping piece as a reference, for the suture needle to be placed on the opposite side therefrom so as to sandwich the other gripping piece.

In the present invention it is also possible for the gripping portion to be provided with an altering device that alters an orientation of the gripping portion such that the gripping portion faces in a direction that intersects the direction of forward or backward movement of the suture needle.

In the present invention it is also possible for there to be provided a supporting sheath that extends in an elongated shape, and, inside the supporting sheath, for the gripping portion and the suture needle to be placed parallel with each other and to be supported so as to be able move forwards or backwards.

Moreover, the present invention includes a gripping portion that grips a tissue piece by sandwiching it; and a suture needle that punctures and sutures the tissue piece, and is supported so as to be able to move forwards or backwards relative to the gripping portion, in which a direction of the forward or backward movement of the suture needle is set in a direction that intersects the tissue piece gripped by the gripping portion.

Moreover, the present invention includes a gripping portion having gripping surfaces that grip a tissue piece by sandwiching it; and a suture needle that punctures and sutures the tissue piece, and is supported so as to be able to move forwards or backwards relative to the gripping portion, in which at least a direction of the forward or backward movement of the suture needle when the suture needle is puncturing the tissue piece is set in a direction that intersects a plane containing the gripping surfaces.

Moreover, the present invention includes a gripping portion that grips a tissue piece by sandwiching it; and a suture needle that punctures and sutures the tissue piece, and is supported so as to be able to move forwards or backwards relative to the gripping portion, in which a space that is capable of receiving a distal end of the suture needle is formed in at least a portion of the gripping portion.

BEST MODE FOR CARRYING OUT THE INVENTION

First Embodiment

The suture instrument according to a first embodiment of the present invention will now be described with reference made to the drawings.

Figure 1:
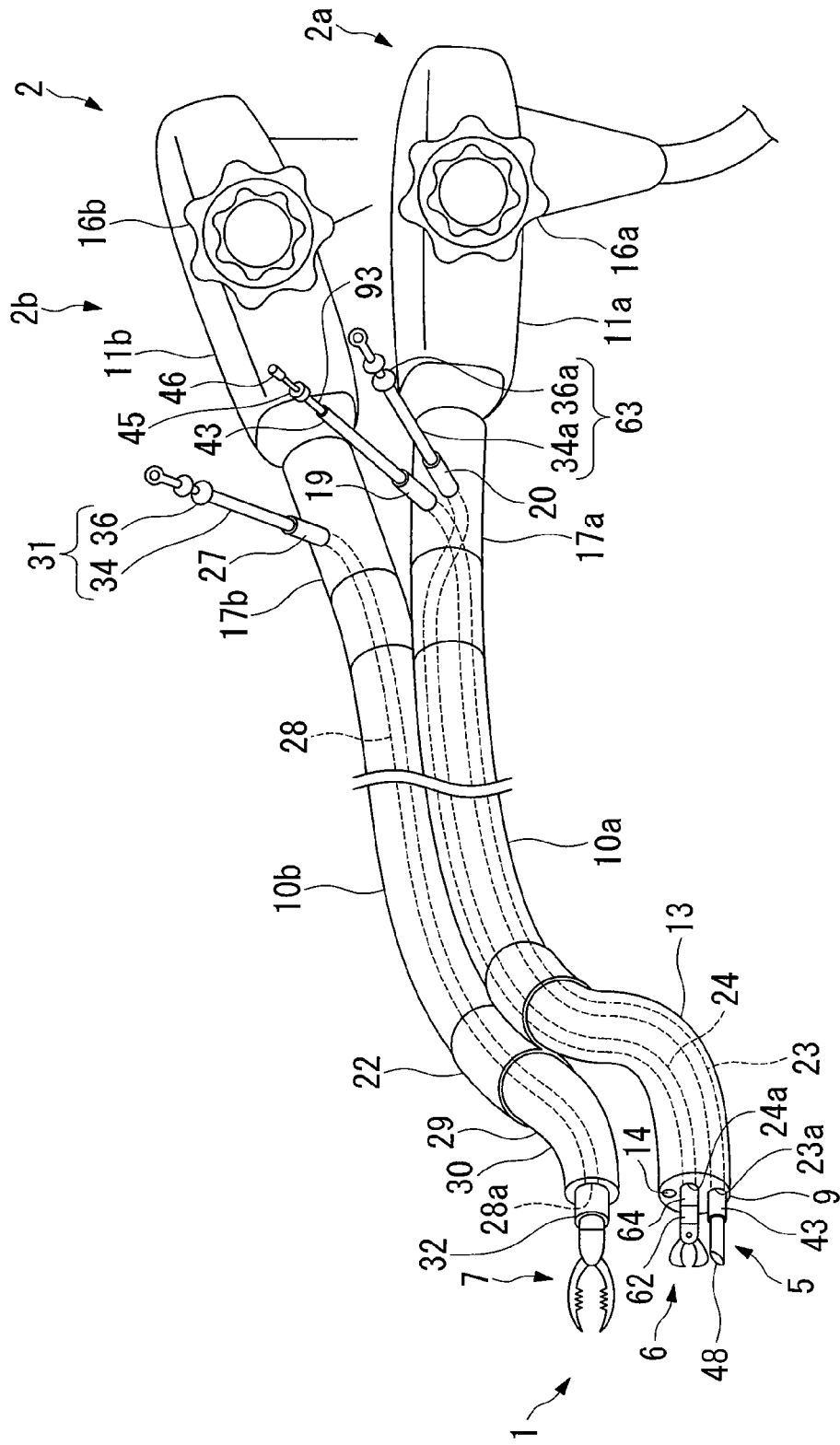
FIG. 1 shows a first embodiment of the suture instrument of the present invention, and is a perspective view showing a state in which a suture instrument is inserted into an endoscope.

As is shown in FIG. 1, a suture instrument 1 of the present embodiment is used together with an endoscope 2 to suture an affected portion.

Therefore, firstly, a description will be given of the endoscope 2 that is used together with the suture instrument 1.

The endoscope 2 is provided with a first endoscope 2a that supports needle forceps 5 and a fastening tool 6 (described below), and a second endoscope 2b that supports gripping forceps 7 (described below). The first endoscope 2a and the second endoscope 2b are constructed so as to be connected by a connecting component 22 while being arranged adjacently to each other.

The first endoscope 2a is provided with an insertion portion 10a that is inserted into a body cavity, and an operating unit 11a that supports the insertion portion 10a. The insertion portion 10a and the operating unit 11a are connected via a connecting portion 17a.

The insertion portion 10a is provided with a bendable bending portion 13. Moreover, a first channel 23 and a second channel 24 are provided inside the insertion portion 10a. Exit aperture portions 23a and 24a that communicate with the first channel 23 and the second channel 24 are provided in a distal end portion 9 of the insertion portion 10a. An observation device 14 that is used to obtain observation images is provided in the vicinity of these exit aperture portions 23a and 24a.

An operating knob 16a that is connected via a wire (not shown) to the bending portion 13 is provided in the operating unit 11a. By manipulating this operating knob 16a it is possible to bend the bending portion 13 up and down and to the left and right and cause the distal end portion 9 to face in a desired direction. Note that the left and right directions refer to the alignment direction in which the insertion portion 10a of the first endoscope 2a and an insertion portion 10b of the second endoscope 2b are placed adjacently to each other. The up and down directions refer to directions that are orthogonal to this alignment direction.

In addition, forcep apertures 19 and 20 are provided in the connecting portion 17a. These forcep apertures 19 and 20 communicate respectively with the exit aperture portions 23a and 24a via the first channel 23 and the second channel 24.

Furthermore, the second endoscope 2b has the same basic structure as the first endoscope 2a, and only points of difference are described here.

The second endoscope 2b is formed as a one-channel scope in which the observation device 14 is not provided. Namely, a channel 28 is provided inside the insertion portion 10b. A forcep aperture 27 is provided at a base end side of the channel 28, while an exit aperture portion 28a is provided at a distal end side thereof.

A two-directional bending portion 29 that is able to bend in the left and right directions, namely, in the directions in which the insertion portion 10b and the insertion portion 10a move towards or away from each other, and a four-directional bending portion 30 that is able to bend up and down and in the left and right directions are provided in the insertion portion 10b.

Next, the suture instrument 1 of the present invention will be described.

The suture instrument 1 is provided with gripping forceps 7, needle forceps 5, and a fastening tool 6.

Figure 2:
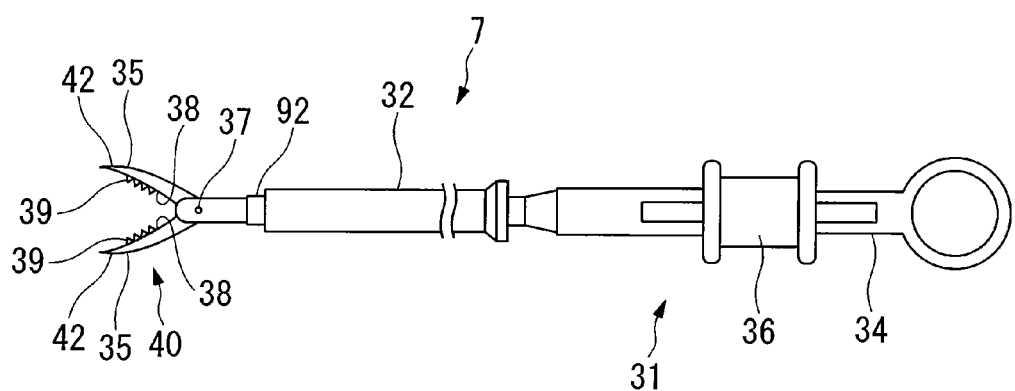
FIG. 2 is a side surface view showing an enlargement of the gripping forceps shown in FIG. 1.
Figure 7:
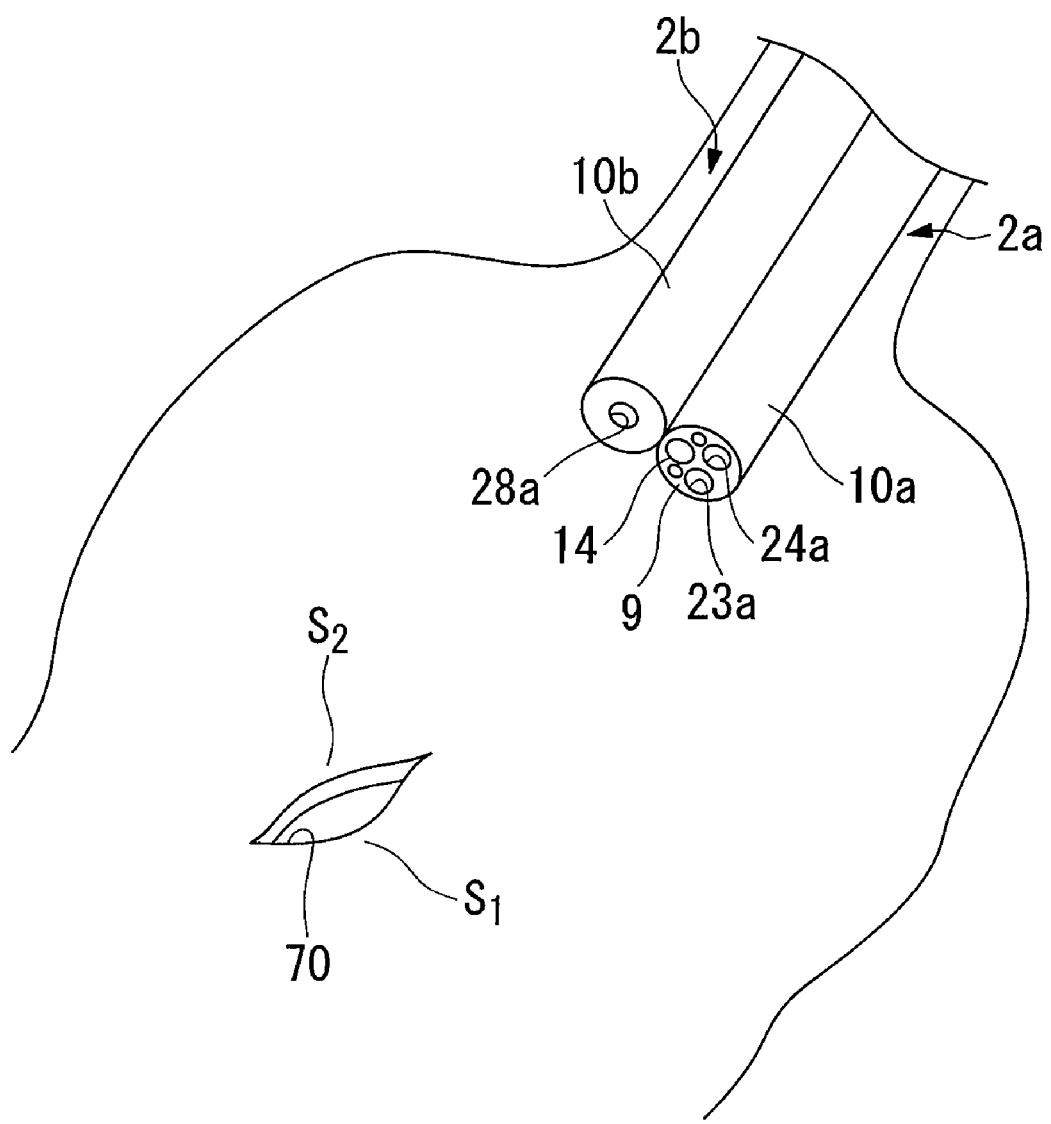
FIG. 7 is an explanatory view showing a state in which an insertion portion of an endoscope is made to approach a tissue opening in a body cavity.

As is shown in FIG. 2, the gripping forceps 7 are provided with a protective sheath 32 that extends in a tube shape, a forceps sheath 92 that passes inside the protective sheath 32, and a gripping forceps operating unit 31 that supports the forceps sheath 92. The forceps sheath 92 is formed by a component that has torque transmission properties such as, for example, a multi-thread coil or a tube containing a mesh. The gripping forceps operating unit 31 is provided with an elongated operating body portion 34 that is connected to the forceps sheath 92, and a slider 36 that is supported such that it can be extended or retracted, and inside which the operating body portion 34 is inserted. A base end portion of an operating wire (not shown) is connected to the slider 36, and a gripping portion 40 that is used to grip a tissue piece is provided at a distal end portion of this operating wire. The gripping portion 40 is provided with gripping pieces 35 that are connected such that they can open and close together around a hinge shaft 37. Gripping surfaces 38 that are used to grip a plurality of tissue pieces $S_1$ and $S_2$ shown in FIG. 7 are formed at locations on the internal side when these gripping pieces 35 are closed together (i.e., at locations where they are superimposed on each other).

The gripping surfaces 38 extend in the longitudinal direction of the gripping pieces 35. In addition, a plurality of projections 39 are provided respectively at positions on the gripping surfaces 38 that face each other when the gripping pieces 35 are closed together. Protruding portions 42 that face in the longitudinal direction of the gripping pieces 35 are provided at distal end portions of the gripping pieces 35. Note that these protruding portions 42 are used in order to make it possible for the plurality of tissue pieces S1 and S2 that are placed at positions facing the gripping portion 40 to be easily gripped. Namely, if the distal end portions of the gripping pieces 35 are made to face each other when the gripping pieces 35 are closed together, then it becomes difficult to clamp the tissue pieces S1 and S2 that are placed in positions facing the gripping portion 40. However, by providing the protruding portions 42, it becomes possible to easily pierce and anchor the tissue pieces S1 and S2 that are located in facing positions. Furthermore, when the gripping portion 40 is inserted into the channel 28 of the second endoscope 2b, the interior wall of the channel 28 can be protected by withdrawing the gripping portion 40 inside the protective sheath 32.

Based on this type of structure, as is shown in FIG. 1, the gripping portion 40 is inserted while in a state of being withdrawn from the forceps aperture 27 into the protective sheath 32. When the protective sheath 32 is fed forward, the gripping forceps 7 are supported such that they are able to move forwards and backwards inside the insertion portion 10b. In addition, if the operating body portion 34 is moved forwards or backwards relative to the forceps aperture 27, the gripping portion 40 is made to appear from the exit aperture portion 28a. If the operating body portion 34 is axially rotated around its axis, the gripping portion 40 is also rotated in the same direction via the forceps sheath 92. Furthermore, by manipulating the slider 36 so that it is moved forwards or backwards while the gripping portion 40 is in a state of protruding from the exit aperture portion 28a, the gripping pieces 35 are made to open or close together via the operating wire. Namely, the gripping pieces 35 move in a direction in which they approach each other and in a direction in which they move apart from each other.

Figure 3:
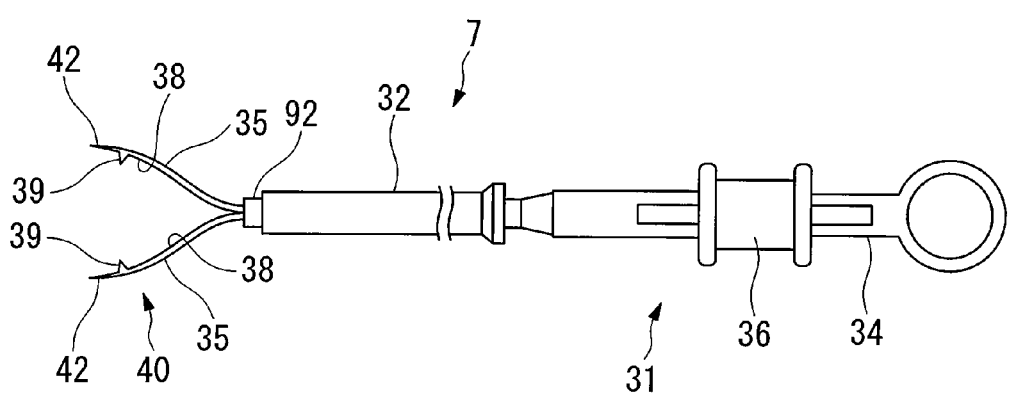
FIG. 3 is a side surface view showing a variant example of the gripping forceps shown in FIG. 2.

Note that the gripping portion 40 is not limited to the structure described above, and may be modified appropriately. For example, as is shown in FIG. 3, it is also possible for the gripping pieces 35 to be formed by elastic components. These gripping pieces 35 are formed such that when they are made to protrude from the forceps sheath 92, the gripping pieces 35 open up from each other. In contrast, when the slider 36 is moved backwards and the gripping pieces 35 are retracted inside the forceps sheath 92, the gripping pieces 35 are elastically deformed and are housed inside the protective sheath 32.

As is shown in FIG. 1, the aforementioned needle forceps 5 are provided with the protective sheath 43 that extends in a tube shape, and a needle sheath 93 is inserted inside the protective sheath 43. A tube-shaped needle knob 45 is provided at a base end portion of the needle sheath 93, and a tube-shaped suture needle 48 that is used to puncture the plurality of tissue pieces S1 and S2 is provided at a distal end portion of the needle sheath 93. A distal end of the suture needle 48 is formed as a sharp pointed portion that slopes at an acute angle, and this makes the puncturing of the tissue pieces S1 and S2 easy. A pusher 49 (see FIG. 4) is inserted into the needle sheath 93, the needle knob 45, and the suture needle 48, and a pusher knob 46 that extends towards the rear from the needle knob 45 is provided at a base end portion of this pusher 49. By moving the pusher knob 46 forwards or backwards relative to the needle knob 45, the pusher 49 is moved forwards or backwards inside the suture needle 48.

Figure 4:
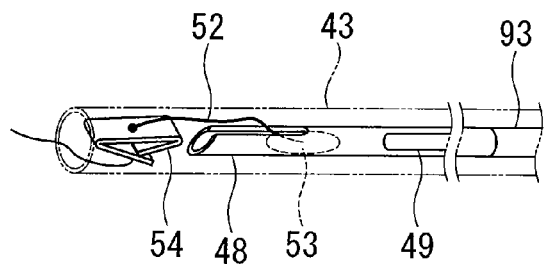
FIG. 4 is a perspective view showing a state in which the suture needle shown in FIG. 1 is placed inside an insertion portion.
Figure 5:
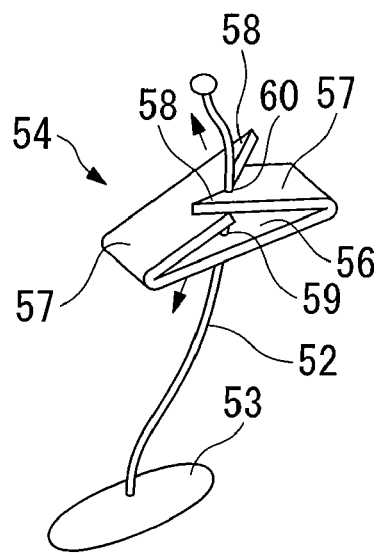
FIG. 5 is an explanatory view showing a state in which the engaging component and the locking component shown in FIG. 4 are connected together.

Furthermore, as is shown in FIGS. 4 and 5, an engaging component 53 that is attached to a suture thread 52 is housed inside the suture needle 48. A locking component 54 is housed inside the protective sheath 43.

The engaging component 53 is formed by a column-shaped component, and a base end of the suture thread 52 which is inserted through biomedical tissue is anchored to the vicinity of the center thereof in the longitudinal direction.

The locking component 54 functions as a lock for the suture thread 52 after suturing. The locking component 54 is provided with a base portion 56 that extends in a plate shape, and two bent pieces 57 that are bent upwards from both ends in the longitudinal direction of the base portion 56 so as to face it at a predetermined angle. The base portion 56 and the bent pieces 57 are integrally connected by elastic components. An aperture portion 59 is formed in the center of the base portion 56. Protruding plates 58 are provided at distal ends of the bent pieces 57 and these two protruding plates 58 are alternately engaged. The suture thread 52 passes through an engagement portion 60 of the two protruding plates 58 and the aperture portion 59, and a distal end of the suture thread 52 that extends from the aperture portion 59 through the engagement portion 60 is left disconnected and free. The engaging component 53 is provided on a base end of the suture thread 52 that extends through the aperture portion 59.

If the suture thread 52 is pulled from the rear end towards the distal end while the locking component 54 is in a fixed state, the two bent pieces 57 are elastically deformed in the direction in which they open outwards. As a result, the engaging portion 60 is expanded which allows the suture thread 52 to move towards the distal end side. If, on the other hand, the suture thread 52 is pulled from the distal end towards the rear end, the two bent pieces 57 are elastically deformed in the direction in which they close together. As a result, the engaging portion 60 is contracted which restricts the movement of the suture thread 52. Namely, if the suture thread 52 is pulled towards the distal end, the locking component 54 moves in a direction in which it approaches the engaging component 53, however, because the movement of the locking component 54 in the direction in which it moves away from the engaging component 53 is restricted, a state in which the two are close to each other is maintained.

Figure 6:
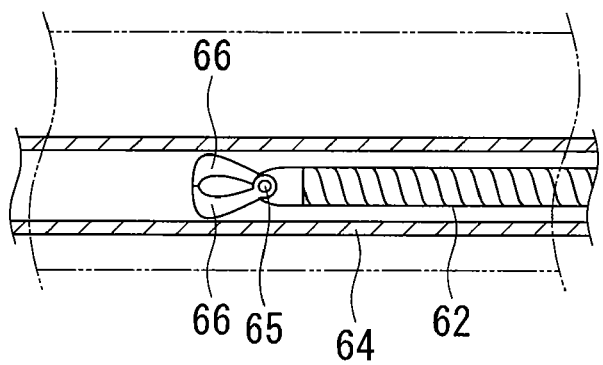
FIG. 6 is an explanatory view showing a state in which the fastening tool shown in FIG. 1 is placed inside a fastening sheath.

As is shown in FIG. 1, the aforementioned fastening tool 6 is provided with a fastening sheath 64 that extends in a tube shape, and a body portion 62 that is inserted inside the fastening sheath 64. A fastening operating unit 63 is provided at a base end portion of the body portion 62. The fastening operating unit 63 is provided with an operating body portion 34a and a slider 36a. Because these have the same structure as the above described operating body portion 34 and slider 36, a description of them is omitted here. As is shown in FIG. 6, nipping pieces 66 that open and close together around a hinge shaft 65 are provided at a distal end of the body portion 62. By moving the slider 36a forwards or backwards, the nipping pieces 66 are made to open or close together via an operating wire.

Based on a structure such as this, as is shown in FIG. 1, if the needle forceps 5 are inserted through the forceps aperture 19 and the fastening tool 6 is inserted through the forceps aperture 20, and if the protective sheath 43 and fastening sheath 64 are fed forward, then the needle forceps 5 and the fastening tool 6 are supported inside the insertion portion 10a such that they can move forwards and backwards. In addition, in the same way as for the gripping forceps 7 described above, if the needle knob 45 and the operating body portion 34a are moved forwards or backwards, the suture needle 48 and the nipping pieces 66 are respectively made to appear from and disappear to the exit aperture portions 23a and 24a. Furthermore, if the needle knob 45 is moved forward by a predetermined amount while the locking component 54 and the engaging component 53 are housed inside the protective sheath 43, firstly, the locking component 54 shown in FIG. 4 is pushed by the suture needle 48 and falls from the distal end of the protective sheath 43. Furthermore, if the pusher knob 46 is then moved forward by a predetermined amount, the engaging component 53 is pushed by the pusher 49 and falls from the distal end of the suture needle 48.

Figure 9:
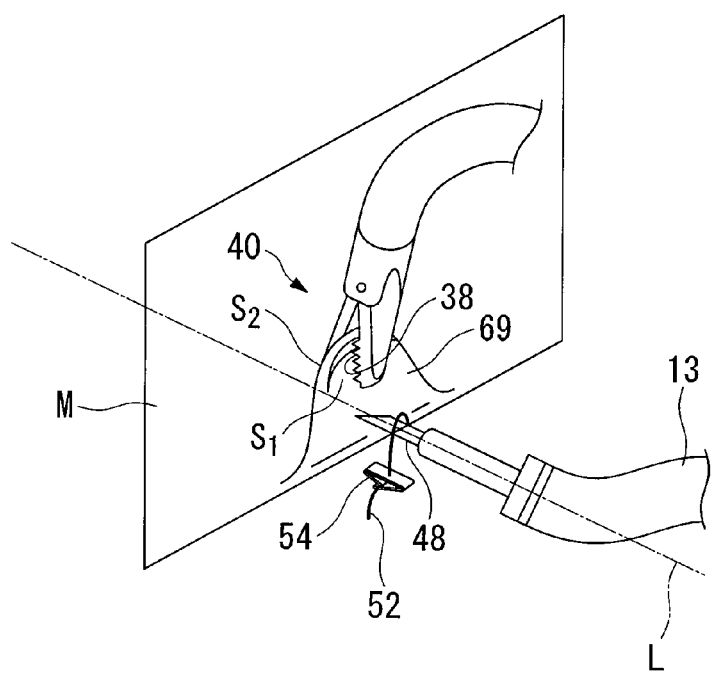
FIG. 9 is an explanatory view showing a state when a suture needle is made to puncture a plurality of tissue pieces that are gripped by the gripping portion.

Furthermore, in the suture instrument 1 of the present embodiment, as is shown in FIG. 9, when the plurality of tissue pieces $S_1$ and $S_2$ are gripped by the gripping portion 40, the plurality of tissue pieces $S_1$ and $S_2$ are lifted up in a state of close contact with the gripping surfaces 38, and the suture needle 48 moves forwards or backwards along an axis L that extends in a direction that intersects a plane M that contains a lifted up tissue wall 69 and the gripping surfaces 38. Namely, a structure is employed in which, when at least this plurality of tissue pieces $S_1$ and $S_2$ are punctured by the suture needle 48 while the plurality of tissue pieces $S_1$ and $S_2$ are being gripped, the plane M and the direction of forwards and backwards movement of the suture needle 48 are orthogonal to each other.

Next, a description will be given of a method of using the suture instrument 1 in the present embodiment that has the above described structure.

In the present embodiment, as is shown in FIG. 7, a description is given using as an example a case in which a tissue opening 70 that is formed in a body cavity is closed and sutured.

Note that portions facing each other on either side of the tissue opening 70 form a plurality of tissue pieces that are divided by the tissue opening 70, and this plurality of tissue pieces are each shown by the symbols $S_1$ and $S_2$.

Figure 8:
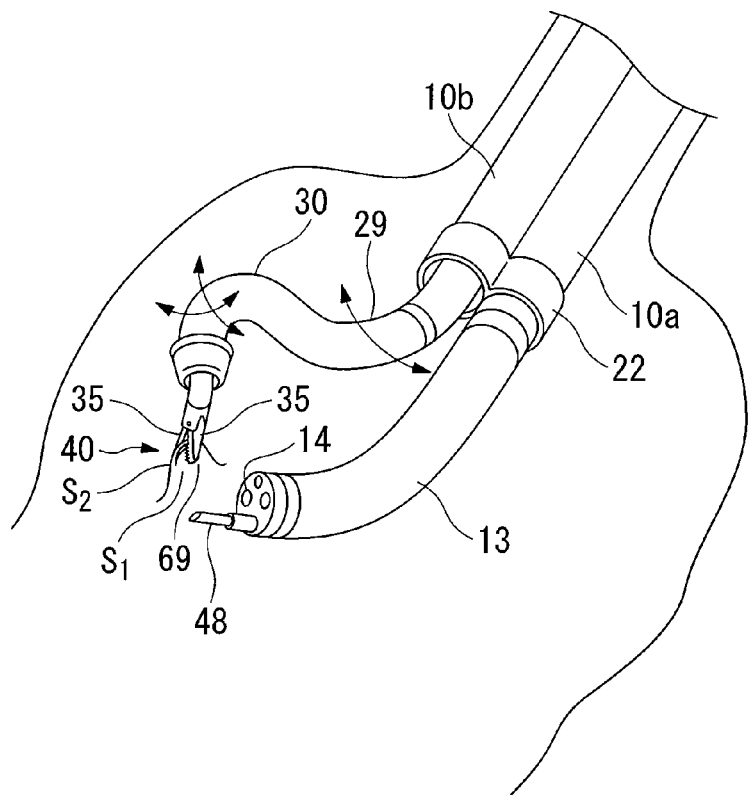
FIG. 8 is an explanatory view showing a state in which a plurality of tissue pieces are gripped by a gripping portion.

Firstly, the gripping forceps 7 are inserted into the insertion portion 10b and, with the locking component 54 and the engaging component 53 housed inside the protective sheath 43, the needle forceps 5 and the fastening tool 6 are inserted into the insertion portion 10a. With each of these left inserted, the insertion portions 10a and 10b are both inserted into the body cavity and fed forward. In addition, while observing observation images that are displayed on a monitor (not shown) via the observation device 14, an operator stops the forward movement of the insertion portions 10a and 10b when the distal end portion 9 has been placed adjacent to the tissue opening 70. From this state, the needle knob 45 and the operating body portion 34 are moved forward, and the suture needle 48 and the gripping portion 40 are made to protrude from the insertion portions 10a and 10b. By then operating an operating knob 16b, as is shown in FIG. 8, the two-directional bending portion 29 is bent in the left direction, namely, in a direction in which it moves away from the insertion portion 10a. The operating knob 16b is then operated again, and the four-directional bending portion 30 is bent in the right direction or in an up-down direction so that the gripping portion 40 is placed next to the tissue opening 70.

At this time, the gripping portion 40 may be rotated via the operating body portion 34 such that the gripping portion 40 is placed in the proper position and angle. By rotating the gripping portion 40, it is possible to alter the direction in which the gripping pieces 35 open and close, namely, to alter the gripping direction. Because of this, when, for example, the tissue opening 70 is formed in a narrow tube or the like and extending in the longitudinal direction thereof, there is a restriction on the direction in which the gripping portion 40 can approach, however, by altering the gripping direction, the tissue opening 70 can be easily closed.

As is described above, after the gripping portion 40 has been placed next to the tissue opening 70, the gripping portion 40 is moved as far as a position where the tissue opening 70 is placed between the gripping pieces 35 that have opened up even further. The slider 36 is then moved backwards while the protruding portions 42 of the gripping pieces 35 are in a state of contact with the respective tissue pieces $S_1$ and $S_2$. As a result, the gripping pieces 35 are closed together and the plurality of tissue pieces $S_1$ and $S_2$ are gripped via the gripping surfaces 38. At this time, the plurality of tissue pieces $S_1$ and $S_2$ are pulled so as to be lifted up. The portions that are thus lifted up form the tissue wall 69.

Figure 10:
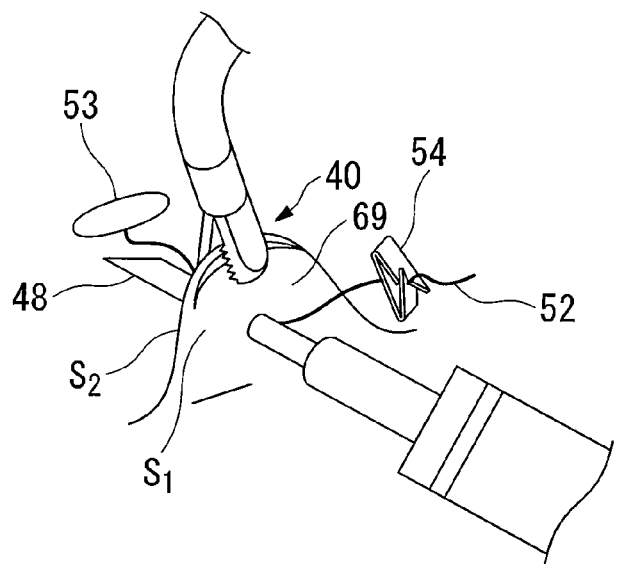
FIG. 10 is an explanatory view showing a state in which a suture needle is made to puncture a plurality of tissue pieces that are gripped by the gripping portion.

Next, the operating knob 16a is operated and, as is shown in FIG. 9, the bending portion 13 is bent in the left direction and in the up-down direction, and the suture needle 48 is moved to a position where the suture needle 48 faces the tissue wall 69. At this time, if the suture needle 48 is moved forwards or backwards via the needle knob 45, the direction of this forwards or backwards movement is aligned with the direction in which the axis L extends and is set so as to be orthogonal to the plane M. From this state, the needle knob 45 is moved forward by a predetermined amount, and the locking component 54 is pushed via the suture needle 48. Accordingly, the locking component 54 is pushed out from the distal end of the protective sheath 43. If the needle knob 45 is moved forward further, the suture needle 48 moves forward along the axis L and, with the locking component 54 remaining on the near side of the tissue wall 69, the suture needle 48 pierces the tissue wall 69. If the suture needle 48 is moved forward further, as is shown in FIG. 10, the suture needle 48 passes through the plurality of tissue pieces $S_1$ and $S_2$, and the distal end of the suture needle 48 protrudes on the distal side of the tissue wall 69.

Figure 11:
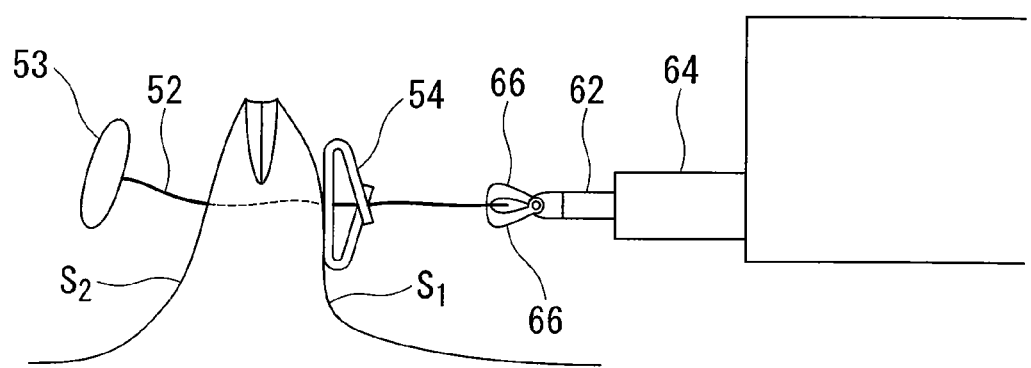
FIG. 11 is an explanatory view showing a state in which a distal end of a suture thread is held by a fastening tool.

While the suture needle 48 is penetrating the plurality of tissue pieces $S_1$ and $S_2$ in this manner, the pusher knob 46 is moved forward and the engaging component 53 is pushed out from the distal end of the suture needle 48. The suture needle 48 is then moved backwards and housed inside the insertion portion 10a. As a result, the suture thread 52 is left behind, and is left in a state of penetrating the plurality of tissue pieces $S_1$ and $S_2$. The engaging component 53 is placed on the distal side of the tissue wall 69 via this suture thread 52, and the locking component 54 is placed on the proximal side. From this state, the operating body portion 34a is moved forward and the nipping pieces 66 are made to protrude from the insertion portion 10a. The nipping pieces 66 are then fed forward until the nipping pieces 66 are placed adjacent to the locking component 54. The slider 36a is then moved backwards so that the nipping pieces 66 are closed together. As a result, as is shown in FIG. 11, the distal end of the suture thread 52 is nipped and the suture thread 52 is consequently held.

Figure 12:
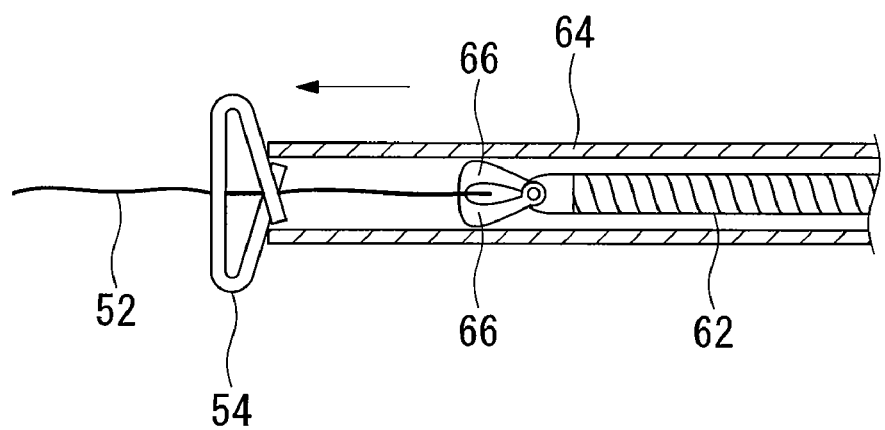
FIG. 12 is an explanatory view showing a state in which a fastening sheath is moved forward so as to move a locking component.
Figure 13:
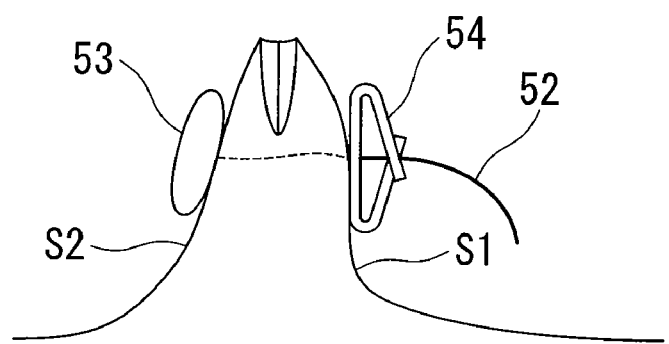
FIG. 13 is an explanatory view showing a state in which a plurality of tissue pieces are sutured by closing off a tissue opening.

From this state, the fastening sheath 64 is moved forwards, and, as is shown in FIG. 12, moves past the nipping pieces 66 and comes against the locking component 54. If the fastening sheath 64 is then moved forward further, with the suture thread 52 remaining in a held state, the locking component 54 is pushed in a direction in which it approaches the engaging component 53. At this time, because the locking component 54 is capable of moving in the direction in which it approaches the engaging component 53, the locking component 54 moves. By then moving the fastening sheath 64 further forward and thereby moving the locking component 54, as is shown in FIG. 13, the plurality of tissue pieces $S_1$ and $S_2$ are tightly nipped between the locking component 54 and the engaging component 53. As a result, the tissue opening 70 is placed in a completely closed state. At this time, because movement of the locking component 54 in a direction away from the engaging component 53 is restricted, the closed state of the tissue opening 70 is maintained. Accordingly, the plurality of tissue pieces $S_1$ and $S_2$ are sutured, and the tissue opening 70 is closed. Finally, the insertion portions 10a and 10b are withdrawn from the body cavity, and the treatment sequence is ended.

As is shown above, according to the suture instrument 1 of the present embodiment, by placing the suture needle 48 in a position where it faces the tissue wall 69 while the plurality of tissue pieces $S_1$ and $S_2$ are gripped by the gripping portion 40, and thereby making the direction of forward movement of the suture needle 48 orthogonal to the plane M, then simply by moving the suture needle 48 forward, the suture needle 48 can be made to easily puncture the plurality of tissue pieces $S_1$ and $S_2$. Consequently, it is possible to easily suture the plurality of tissue pieces $S_1$ and $S_2$ using the engaging component 53, the locking component 54, and the suture thread 52. Furthermore, because it is possible using the locking component 54 to not only reliably maintain a state in which the tissue opening 70 is closed for an extended period of time, but also provide treatment using a flexible endoscope, the burden on a patient can be greatly reduced.

Note that in the present embodiment, the first endoscope 2a is provided with multiple channels, while the second endoscope 2b is provided with one channel, however, the present invention is not limited to this, and these combinations may be modified as is appropriate. For example, it is also possible for the gripping forceps 7 and the fastening tool 6 to be inserted in the first endoscope 2a. It is also possible for the first endoscope 2a to be provided with one channel, and to insert the needle forceps 5 therein. After the plurality of tissue pieces $S_1$ and $S_2$ have been punctured, the needle forceps 5 are withdrawn, and the fastening tool 6 is then inserted into that channel.

It is also possible to not use two endoscopes, but instead provide an external bending channel in the first endoscope 2a.

Furthermore, in the present embodiment, the fastening tool 6 is used, however, the present invention is not limited to this and it is also possible to not provide the fastening tool 6. In this case, the suture thread 52 may be extended as far as the near side and held there.

Moreover, the two-directional bending portion 29 is provided in the second endoscope 2b, however, the present invention is not limited to this and the two-directional bending portion 29 may be provided in at least one of the first endoscope 2a or the second endoscope 2b.

Figure 14:
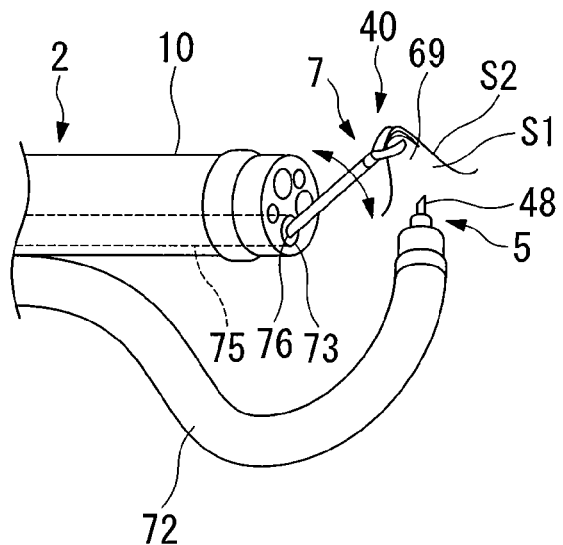
FIG. 14 shows a variant example of the endoscope shown in FIG. 1, and is an explanatory view showing a state in which an external bending channel is used.

Furthermore, although the two-directional bending portion 29 is provided, the structure that causes the gripping portion 40 and the suture needle 48 to move towards or away from each other is not limited to this and various modifications are possible. For example, as is shown in FIG. 14, it is also possible to insert the gripping forceps 7 in a channel 75, and provide an upward director 73 in the exit aperture portion 76. Note that, in FIG. 14, an example is shown in which the needle forceps 5 are inserted into an external bending channel 72.

Figure 15:
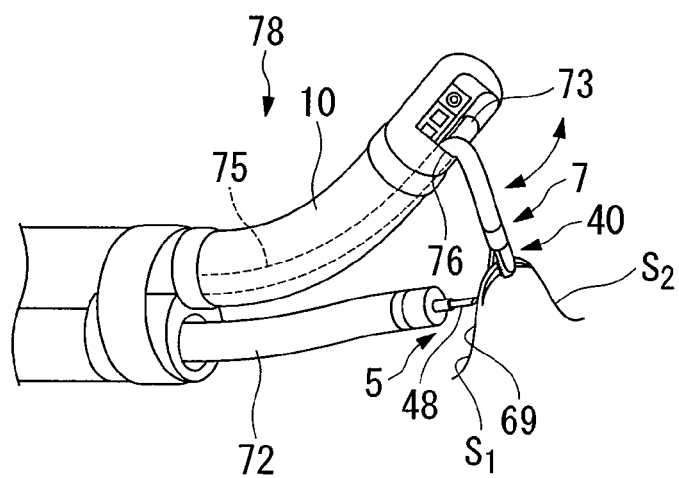
FIG. 15 shows a variant example of the endoscope shown in FIG. 1, and is an explanatory view showing a state in which a side view endoscope is used.

Furthermore, a case has been described in which a direct-view type of endoscope is used, however, the present invention is not limited to this and, for example, as is shown in FIG. 15, it is also possible to use a side-view or diagonal-view endoscope 78. Note also that, in FIG. 15, in the same way as in FIG. 14, the upward director 73 is provided in the exit aperture portion 76 so that the gripping portion 40 and the suture needle 48 can be made to approach or move apart from each other, and the external bending channel 72 is used.

Figure 16:
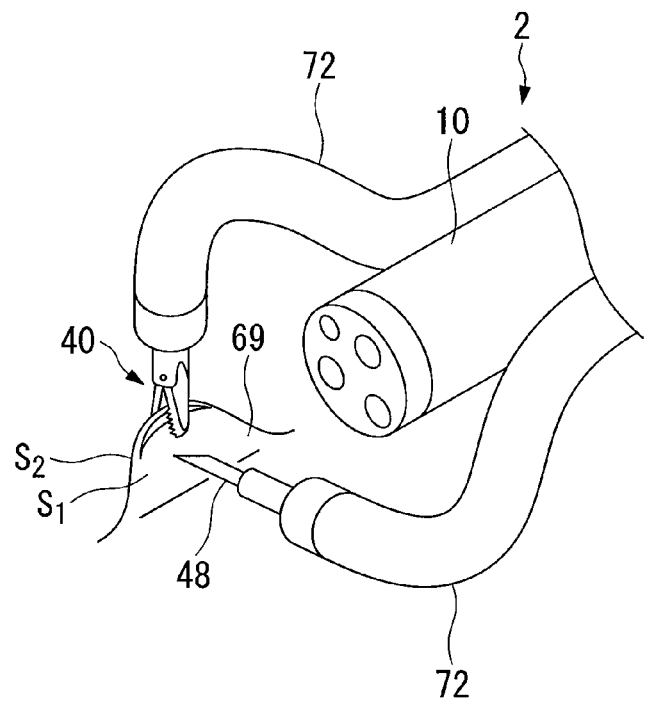
FIG. 16 shows a variant example of the endoscope shown in FIG. 1, and is an explanatory view showing a state in which two external bending channels are used.

Moreover, for example, as is shown in FIG. 16, it is also possible to use a plurality of external bending channels 72. This makes a higher level of treatment possible.

Figure 17:
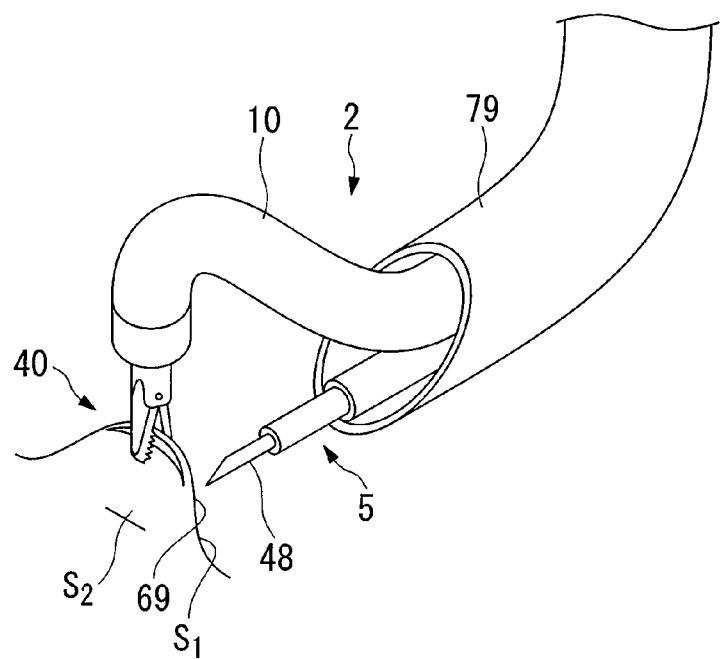
FIG. 17 shows a variant example of the endoscope shown in FIG. 1, and is an explanatory view showing a state in which a guide tube is used.

Furthermore, for example, as is shown in FIG. 17, it is also possible to use a guide tube 79 that has a forceps channel. Note that, in FIG. 17, a state is shown in which the endoscope portion 10 and the needle forceps 5 of the endoscope 2 are inserted into the guide tube 79, however, the present invention is not limited to this and this combination may be appropriately modified such as by inserting the needle forceps 5 into the insertion portion 10.

Second Embodiment

Next, the second embodiment of the present invention will be described.

Figure 18:
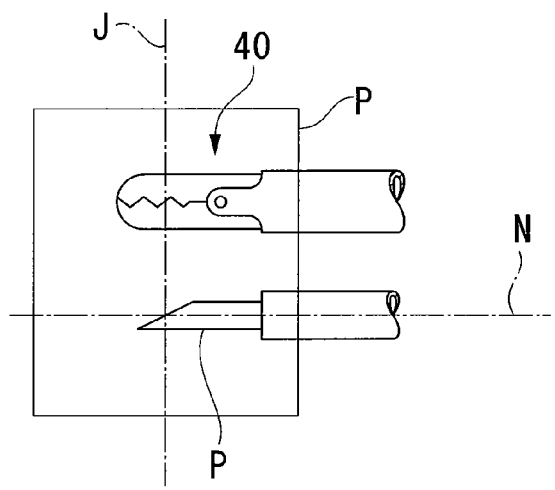
FIG. 18 is an explanatory view showing principal portions of a second embodiment of the suture instrument of the present invention.
Figure 19:
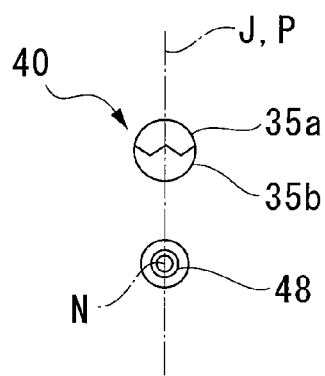
FIG. 19 is a front view showing the gripping portion and suture needle shown in FIG. 18.

FIG. 18 and FIG. 19 show the second embodiment of the present invention.

In FIG. 18 and FIG. 19, portions that are the same as component elements already described in FIG. 1 through FIG. 17 are given the same symbols and a description thereof is omitted.

In the above described first embodiment, the positional relationship between the gripping portion 40 and the suture needle 48 is not particularly restricted, however, in the present embodiment, the positional relationship between the two is clearly defined.

Namely, as is shown in FIGS. 18 and 19, when the suture needle 48 is being inserted into a body cavity, it is positioned such that the direction of the forward or backward movement thereof is parallel with the direction of forward or backward movement of the gripping portion 40. In addition, the suture needle 48 is positioned on the same plane as a plane containing a virtual line J that extends in the direction in which the one gripping piece 35*a* and the other gripping piece 35*b* move towards or away from each other, and an axis N that extends in the direction of forward or backward movement of the suture needle 48 when it is being inserted. Furthermore, the suture needle 48 is placed on the plane P and, taking the one gripping piece 35*a* as a reference, is placed on the opposite side from the gripping piece 35*a* so as to sandwich the other gripping piece 35*b*.

As a result, without placing the suture needle 48 on the same axis as the gripping portion 40, it is possible to reliably puncture the plurality of tissue pieces $S_1$ and $S_2$ that are gripped by the gripping portion 40.

Note that, in the present embodiment, one each of the gripping portion 40 and the suture needle 48 are provided respectively, however, the present invention is not limited to this and the number employed of each can be appropriately modified.

Figure 20:
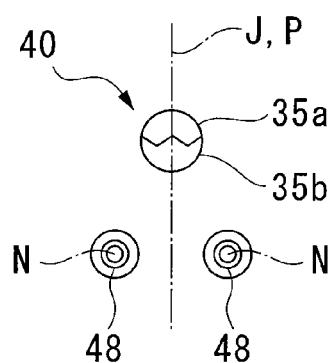
FIG. 20 shows a variant example of the gripping portion and suture needle shown in FIG. 19, and is an explanatory view showing a state in which two suture needles are provided.

For example, as is shown in FIG. 20, it is also possible to provide two suture needles 48. Namely, during the aforementioned insertion, the two suture needles 48 are placed facing each other on substantially the same plane as the plane P.

Figure 21:
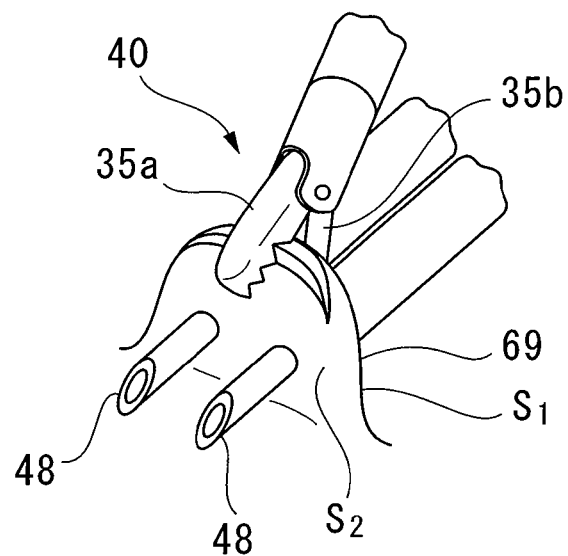
FIG. 21 shows a plurality of tissue pieces gripped by the gripping portion shown in FIG. 20, and is an explanatory view showing a state in which puncturing is performed by two suture needles.

As a result, as is shown in FIG. 21, a plurality of suture needles 48 can be made to puncture the plurality of tissue pieces $S_1$ and $S_2$, and it is possible to firmly and reliably close the tissue opening 70.

Figure 22:
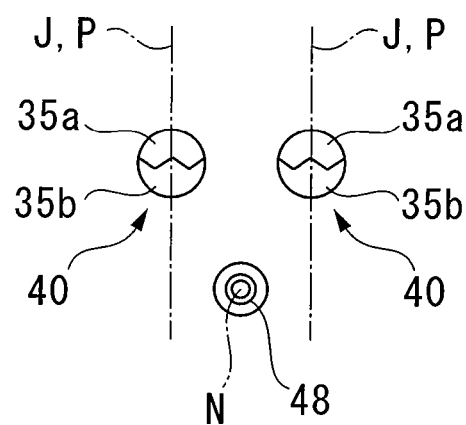
FIG. 22 shows a variant example of the gripping portion and suture needle shown in FIG. 19, and is an explanatory view showing a state in which two gripping portions are provided.

Moreover, for example, as is shown in FIG. 22, it is also possible to provide two gripping portions 40. Namely, during the aforementioned insertion, the two gripping portions 40 are placed facing each other on substantially the same plane as the plane P.

Figure 23:
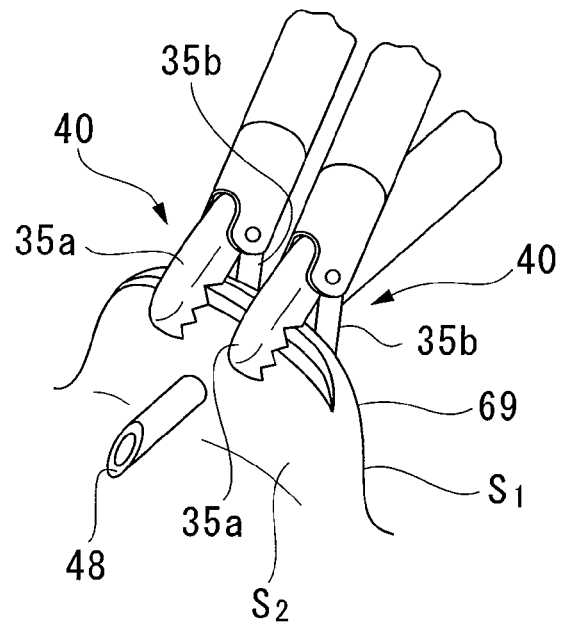
FIG. 23 is an explanatory view showing a state in which a suture needle is made to puncture a plurality of tissue pieces gripped by the two gripping portions shown in FIG. 22.

As a result, as is shown in FIG. 23, the plurality of tissue pieces $S_1$ and $S_2$ can be firmly and reliably gripped by the two gripping portions 40, and the suture needle 48 can be made to penetrate easily.

Third Embodiment

Next, the third embodiment of the present invention will be described.

Figure 24:
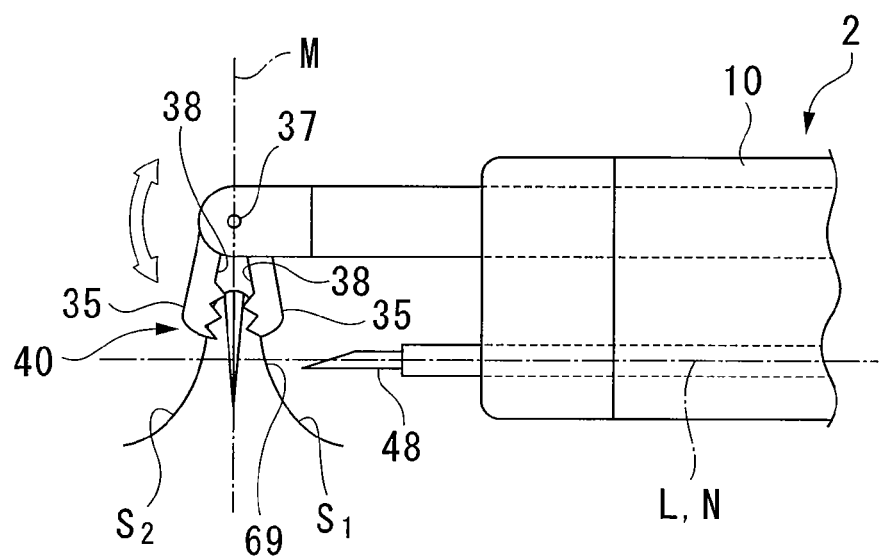
FIG. 24 is a side surface view showing principal portions of a third embodiment of the suture instrument of the present invention.

FIG. 24 shows the third embodiment of the present invention.

This embodiment has the same basic structure as that of the above described second embodiment and the points described below are points of variance.

Namely, in the present embodiment, not only are the gripping pieces 35 formed so as to be able to open and close together by pivoting on the hinge shaft 37, but, as is shown in FIG. 24, these gripping pieces 35 are able to rotate as a single unit around the hinge shaft 37. Furthermore, the gripping portion 40 is urged by an urging component (not shown) so as to rotate around the hinge shaft 37 and face the side where the suture needle 48 is positioned. As a result, while the gripping portion 40 is being housed in the insertion portion 10, the gripping portion 40 is positioned such that the gripping pieces 35 face in the direction of forward and backward movement of the gripping portion 40. However, if the gripping portion 40 is made to protrude from the insertion portion 10, then the gripping portion 40 rotates and faces the side where the suture needle 48 is located. At this time, the gripping surfaces 38 are placed at positions that substantially faces the suture needle 48, the plane M that contains the gripping surfaces 38 and the axis N that extends in the direction of forward or backward movement of the suture needle 48, when it is being inserted, are orthogonal to each other. Note that in the present embodiment the hinge shaft 37 functions as an altering device that alters the orientation of the gripping portion 40.

Based on a structure such as that described above, the gripping portion 40 is made to protrude from the insertion portion 10, and the gripping portion 40 is then rotated. When the plurality of tissue pieces $S_1$ and $S_2$ that are located at a position facing the gripping portion 40 are gripped, the tissue wall 69 is located at a position facing the suture needle 48, namely, in front of the suture needle 48. Therefore, if the suture needle 48 is moved forward, the suture needle 48 advances along the axis L and punctures the plurality of tissue pieces $S_1$ and $S_2$.

As a result, simply by gripping the plurality of tissue pieces $S_1$ and $S_2$ using the gripping portion 40, the suture needle 48 can be made to move easily along the axis L. Moreover, the axis L during puncturing and the axis N during insertion can be matched to each other so that suturing is simplified still further.

Figure 25:
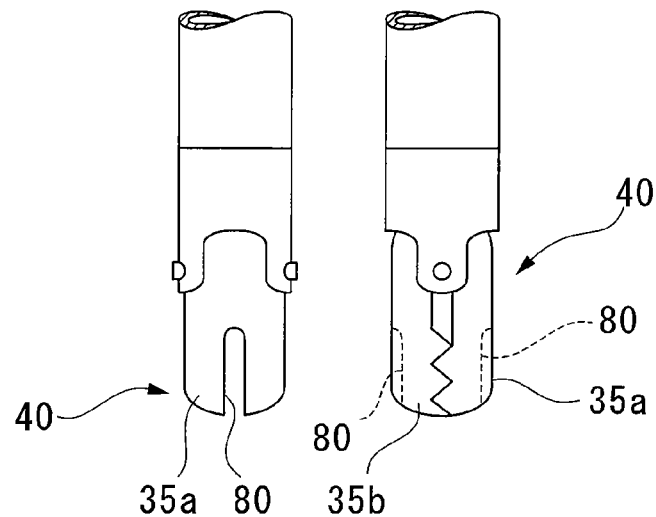
FIG. 25 shows a variant example of the gripping piece shown in FIG. 24, and is an explanatory view showing a state in which a notch is provided in the gripping piece.
Figure 26:
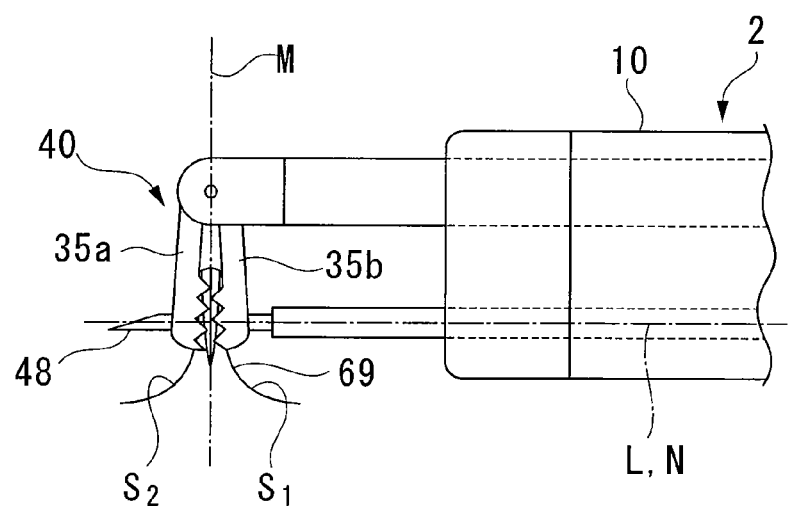
FIG. 26 is an explanatory view showing a state in which a plurality of tissue pieces gripped by the gripping piece shown in FIG. 25 are punctured via the notch.

Note that the shape of the gripping portion 40 can be appropriately modified. For example, as is shown in FIG. 25, it is also possible to form a notch 80 that extends in the longitudinal direction of the gripping pieces 35*a* and 35*b* on each of the gripping pieces 35*a* and 35*b*. If, as is shown in FIG. 26, the suture needle 48 is moved forward while the plurality of tissue pieces $S_1$ and $S_2$ are being gripped by the gripping portion 40, the suture needle 48 advances inside the notch 80.

As a result, because it is possible to make a suture extremely close to the open portion of the plurality of tissue pieces $S_1$ and $S_2$, the biomedical tissue does not have to be greatly stretched and the burden on the tissue can be reduced. Moreover, it is possible to prevent blood from inflowing inside the suture portion and then leaking out.

Figure 27:
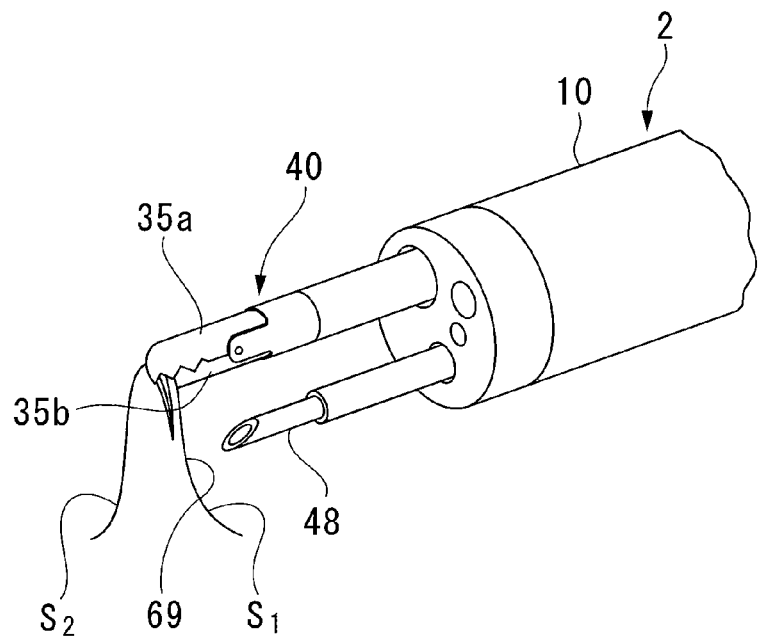
FIG. 27 is an explanatory view showing a state in which the gripping portion shown in FIG. 24 is moved backwards as far as the distal end of the insertion portion while a plurality of tissue pieces are being gripped.

Moreover, in the present embodiment, the suture needle 48 is made to penetrate with the gripping portion 40 in a state of facing the suture needle 48 side, however, the present invention is not limited to this. For example, as is shown in FIG. 27, it is also possible to pull the gripping portion 40 while it is gripping the plurality of tissue pieces $S_1$ and $S_2$ into the insertion portion 10, and make the gripping pieces 35a and 35b face in the direction of forward and backward movement of the gripping portion 40. This enables the plurality of tissue pieces $S_1$ and $S_2$ to be stretched and enables the tissue wall 69 to be reliably placed in front of the suture needle 48. Accordingly, the plurality of tissue pieces $S_1$ and $S_2$ can be reliably punctured.

Furthermore, in the present embodiment, the gripping portion 40 is rotated around the hinge shaft 37, however, the present invention is not limited to this and the structure thereof may be appropriately modified. For example, it is also possible to employ a structure in which a permanent bend is formed in the protective sheath 32 so that, when the gripping portion 40 is made to protrude from the insertion portion 10, the gripping portion 40 is made to protrude on the suture needle 48 side by the protective sheath 32.

Fourth Embodiment

Next, the fourth embodiment of the present invention will be described.

FIGS. 28 through 31 show the fourth embodiment of the present invention.

This embodiment has the same basic structure as that of the above described second embodiment and the points described below are points of variance.

Figure 28:
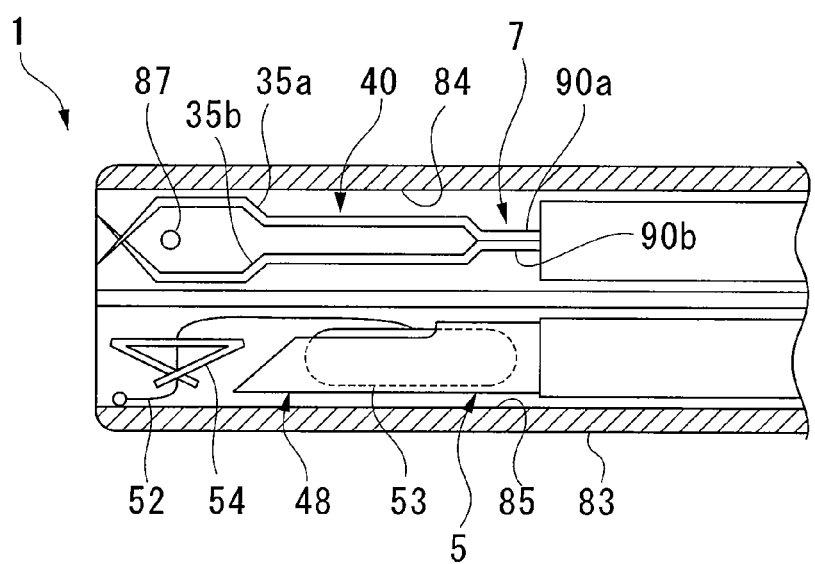
FIG. 28 is a transparent side surface view showing principal portions of a fourth embodiment of the suture instrument of the present invention

As is shown in FIG. 28, the suture instrument 1 of the present embodiment is provided with an elongated supporting sheath 83. A gripping forceps insertion channel 84 and a needle forceps insertion channel 85 are formed inside this supporting sheath 83, and the gripping forceps 7 and the needle forceps 5 are inserted respectively therein. A rod-shaped component 87 that runs in a direction that is orthogonal to the direction of forward and backward movement of the gripping forceps 7 is provided in the vicinity of the distal end portion of the gripping forceps insertion channel 84.

Figure 29:
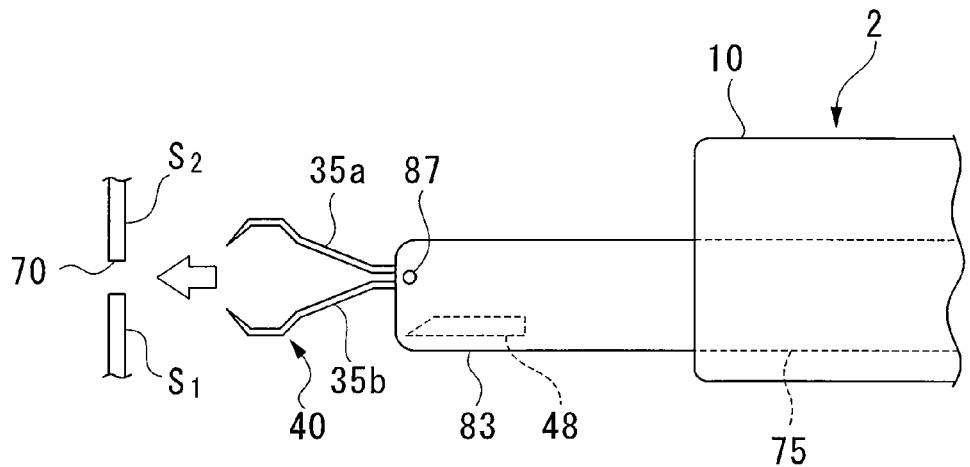
FIG. 29 is an explanatory view showing a state in which the gripping portion shown in FIG. 28 is moved forwards towards a tissue opening.

The supporting sheath 83 supports the gripping forceps 7 and the needle forceps 5 such that they can move forwards and backwards while being held parallel with each other. While supporting the gripping forceps 7 and the needle forceps 5 in this manner, as is shown in FIG. 29, the supporting sheath 83 is inserted into the channel 75 of the endoscope 2.

Furthermore, joining portions 90a and 90b that join together when the gripping pieces 35a and 35b are closed are provided at base end portions of the gripping pieces 35a and 35b. In contrast, distal end portions of the gripping pieces 35a and 35b are formed in a hook shape and, when these gripping pieces 35a and 35b are closed together, the distal ends cross over each other. When the gripping pieces 35a and 35b are closed together inside the distal end portion of the gripping forceps insertion channel 84, the rod-shaped component 87 is located between the gripping pieces 35a and 35b.

When the gripping portion 40 is made to protrude from the distal end of the supporting sheath 83 and is moved forward by a predetermined amount, the rod-shaped component 87 is positioned between the joining portions 90a and 90b. As a result, the gripping pieces 35a and 35b are opened up from each other.

Figure 30:
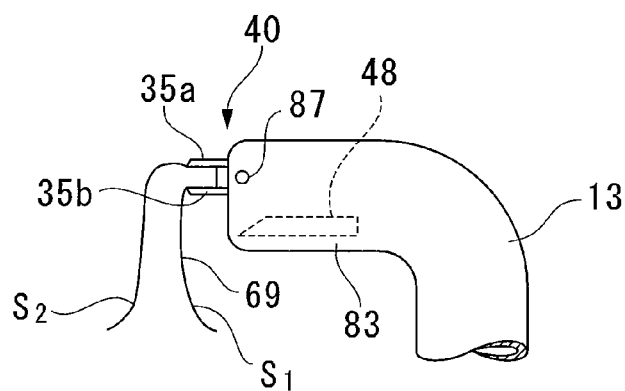
FIG. 30 is an explanatory view showing a state in which a plurality of tissue pieces are gripped by the gripping portion shown in FIG. 28, and a tissue wall is made to face a suture needle.
Figure 31:
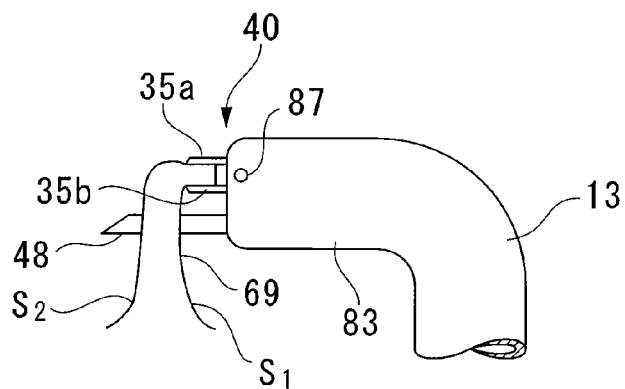
FIG. 31 is an explanatory view showing a state in which a plurality of tissue pieces are gripped by the gripping portion shown in FIG. 28, and are punctured by a suture needle.

Based on a structure such as this, the gripping portion 40 is moved forward as far as a position where it faces the tissue opening 70 of the gripping portion 40. The distal ends of the gripping pieces 35a and 35b are then placed in contact with the plurality of tissue pieces $S_1$ and $S_2$, and the gripping pieces 35a and 35b are then both closed up. While the plurality of tissue pieces $S_1$ and $S_2$ are still being gripped, as is shown in FIG. 30, the gripping portion 40 is pulled back inside the insertion portion 10 and the bending portion 13 is bent in a predetermined direction. The bend state of the bending portion 13 is then adjusted so that the tissue wall 69 is positioned in front of the suture needle 48. In this state, if the suture needle 48 is moved forward, as is shown in FIG. 31, it punctures the plurality of tissue pieces $S_1$ and $S_2$.

Accordingly, because it is possible to insert the gripping forceps 5 and the needle forceps 7 in a single channel 75 of the endoscope 2, the gripping forceps 5 and the needle forceps 2 can be positioned adjacent to each other, and it is possible to puncture and form a suture extremely close to the open portion of the plurality of tissue pieces $S_1$ and $S_2$. Moreover, while the insertion portion 10 is still inserted inside the body cavity, simply by withdrawing and inserting the supporting sheath 83, the suture instrument 1 can be easily inserted and withdrawn.

Note that in the above described first through fourth embodiments, a description has been given of treatment to cover the tissue opening 70, however, the present invention is not limited to this and may be applied to any treatment to suture a plurality of tissue pieces. For example, it is also possible to suture together creases that are formed in a stomach wall or the like as a plurality of tissue pieces.

Moreover, the direction of forward movement of the suture needle 48 during insertion is set to be orthogonal with the plane M, however, the present invention is not limited to this and this angle may be appropriately modified within a range in which it intersects the plane M.

Note that the technical range of the present invention is not limited by the above described embodiment and various modifications can be made without departing from the spirit or scope of the present invention.

The present invention includes a gripping portion that grips a plurality of tissue pieces by sandwiching them, and a suture needle that punctures and sutures the plurality of tissue pieces. The suture needle is supported so as to be able to move forwards or backwards relative to the gripping portion, and the direction of the forward or backward movement of the suture needle is set to a direction that intersects the tissue pieces gripped by the gripping portion.

In the suture instrument according to the present invention, a plurality of tissue pieces are gripped by a gripping portion, and a suture needle is moved forwards or backwards relative to the gripping portion in a direction which intersects the gripped tissue pieces.

As a result, simply by moving the suture needle forwards while the plurality of tissue pieces are being gripped, it is possible to make the suture needle easily penetrate the plurality of tissue pieces.

The present invention includes a gripping portion having gripping surfaces that grip a plurality of tissue pieces by sandwiching them, and a suture needle that punctures and sutures the plurality of tissue pieces. The suture needle is supported so as to be able to move forwards or backwards relative to the gripping portion, and a direction of the forward or backward movement of the suture needle at least when it is puncturing the tissue pieces is set to a direction that intersects a plane containing the gripping surfaces.

In the suture instrument according to the present invention, a plurality of tissue pieces are gripped by gripping surfaces that are provided in a gripping portion, and a suture needle is moved forwards or backwards relative to the gripping portion. At this time, because the direction of the forward or backward movement of the suture needle at least when it is puncturing the tissue pieces is set to a direction that intersects a plane containing the gripping surfaces, if the suture needle is moved forward relative to the gripping portion from a predetermined position while the plurality of tissue pieces are being gripped, the suture needle is moved forward in a direction which intersects the gripped tissue pieces.

As a result, simply by moving the suture needle forwards while the plurality of tissue pieces are being gripped, it is possible to make the suture needle easily penetrate the plurality of tissue pieces.

In the present invention, the gripping portion is provided with gripping pieces on which the gripping surfaces are respectively provided. These gripping pieces are able to move in a direction in which they approach each other and in a direction in which they move apart from each other. When these gripping pieces are made to approach each other and grip the tissue pieces via the gripping surfaces, at least one of the gripping surfaces is placed at a position facing the suture needle.

In the suture instrument according to the present invention, if the gripping pieces are made to approach each other and grip the tissue pieces via the gripping surfaces, at least one of the gripping surfaces is placed at a position facing the suture needle.

As a result, simply by gripping the plurality of tissue pieces, it is possible to make the suture needle move forward easily in a direction which intercepts the gripped tissue pieces.

In the present invention, the suture needle is located on substantially the same plane as a plane containing a virtual line that extends in a direction in which the plurality of gripping pieces move towards or apart from each other, and an axis that extends in the direction of forward or backward movement of the suture needle. Taking one gripping piece as a reference, the suture needle is placed on the opposite side therefrom so as to sandwich the other gripping piece.

In the suture instrument of the present invention, the suture needle punctures a portion of the plurality of tissue pieces, which are gripped via the gripping surface, that is located on substantially the same plane.

As a result, the gripped plurality of tissue pieces can be reliably punctured without the tissue needle having to be positioned coaxially with the gripping portion.

The present invention is provided with an altering device that alters an orientation of the gripping portion such that the gripping portion faces in a direction that intersects the direction of forward or backward movement of the suture needle.

In the suture instrument according to the present invention, the gripping portion is made to face in a direction that intersects the direction of forward or backward movement of the suture needle by the altering device. If the gripping portion is then moved forward so that it grips the plurality of tissue pieces to the front of where it is facing, the suture needle ends up facing the plurality of tissue pieces. Alternatively, if the gripping portion is moved backwards as far as the sheath while it is still gripping the plurality of tissue pieces, the plurality of tissue pieces become stretched and the suture needle ends up facing the plurality of tissue pieces.

As a result, the plurality of tissue pieces can be easily gripped and the gripped plurality of tissue pieces can be reliably punctured.

The present invention is provided with a supporting sheath that extends in an elongated shape, and, inside the supporting sheath, the gripping portion and the suture needle are placed parallel with each other and are supported so as to be able move forwards or backwards.

In the suture instrument according to the present invention, the gripping portion and the suture needle are placed parallel with each other and are supported by the supporting sheath so as to be able move forwards or backwards.

As a result, the gripping portion and the suture needle can be reliably inserted into a body cavity. Moreover, while the endoscope is inserted inside a body cavity, the gripping portion and suture needle can be easily inserted or pulled out without the endoscope being withdrawn. Furthermore, because the gripping portion and the suture needle are adjacent to each other inside the supporting sheath, it is possible to puncture an area of the plurality of gripped tissue pieces that is extremely close to the gripping portion.

The invention claimed is:

1. A gripping instrument comprising:
an insertion portion which has a longitudinal axis;
a gripping portion that is configured to grip a tissue piece by sandwiching the tissue piece, the gripping portion positioned at a distal end side of the insertion portion, the gripping portion comprising a pair of gripping pieces positioned to face each other so as to approach and move apart freely from each other, the gripping pieces being configured to rotate as a unit relative to the longitudinal axis;
an operating unit which is provided at a proximal end side of the insertion portion and is configured to operate the approaching and moving apart of the pair of gripping pieces;
a needle member which is provided so as to move relative to the gripping portion, and
a pair of slits positioned to penetrate the pair of gripping pieces along an axis traversing the pair of gripping pieces, the pair of slits being formed so that the slits face each other and are notched to a same direction, the pair of slits extending in a radial direction of the gripping portion from the axis traversing the pair of gripping pieces to outside of an exterior of the gripping portion, wherein
the needle member is configured to penetrate the pair of slits along the axis traversing the pair of gripping pieces.

* * * * *